United States Patent
Carlini et al.

[11] 4,036,733
[45] July 19, 1977

[54] FLUORESCENT BENZANTHRONIC DYES

[75] Inventors: Filippo Maria Carlini, Novara; Giampiero Pieri, Saronno (Varese); Camillo Paffoni, Pogno (Novara); Gioacchino Boffa, Novara, all of Italy

[73] Assignee: Montedison Fibre S.p.A., Milan, Italy

[21] Appl. No.: 679,029

[22] Filed: Apr. 21, 1976

[30] Foreign Application Priority Data

Apr. 24, 1975 Italy ........................... 22722/75

[51] Int. Cl.² .......... C10G 41/00; C10L 1/24; C07D 235/04; C08K 5/16
[52] U.S. Cl. .......................... 208/12; 44/59; 260/37 PC; 260/42.21; 260/309.2
[58] Field of Search .......... 44/59; 260/309.2, 37 PC, 260/42.21; 204/73 R; 252/301.2

[56] References Cited

U.S. PATENT DOCUMENTS

| | | | |
|---|---|---|---|
| 1,824,977 | 9/1931 | Allerman | 44/59 |
| 2,071,481 | 2/1937 | Winning et al. | 208/12 |
| 2,074,288 | 3/1937 | Tinker et al. | 44/59 X |
| 2,538,313 | 1/1951 | Holbro et al. | 260/309.2 X |
| 2,967,862 | 1/1961 | Berry et al. | 44/59 X |
| 3,114,633 | 12/1963 | Schlesinger | 260/309.2 X |
| 3,772,321 | 11/1973 | Zickendraht | 260/309.2 |

OTHER PUBLICATIONS

Def. Pub. No. T878,023 Taylor et al., published 9/29/70.

*Primary Examiner*—F.C. Edmundson
*Attorney, Agent, or Firm*—Stevens, Davis, Miller & Mosher

[57] ABSTRACT

A plastosoluble fluorescent organic dye is disclosed that is derived from benzanthrone, and having the general formula:

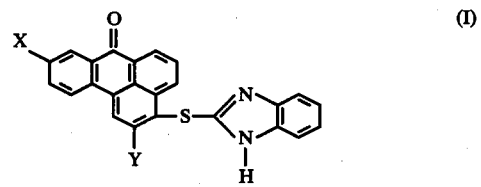

(I)

wherein X = —H or —Br; and Y = —H, —OCH₃ or —OC₂H₅. A process for the preparation of a dye of the general formula (I) is also disclosed. These dyes are useful in the bulk dyeing of polystyrene, polymethylmethacrylate, rigid PVC, polyethylene, acrylonitrile-/butadiene/styrene copolymers, polycarbonates or mineral oils.

10 Claims, No Drawings

FLUORESCENT BENZANTHRONIC DYES

The present invention relates to new fluorescent organic dyes derived from benzanthrone, and having the general formula:

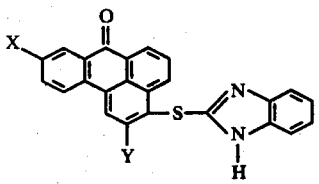

(I)

wherein
X = —H or Br; and
Y = —H, —OCH₃ or —OC₂H₅

These dyes are useful for the bulk dyeing of polystyrene, polymethylmethacrylate, rigid polyvinylchloride (PVC), polyethylene, ABS polymers (acrylonitrile-/butadiene/styrene), polycarbonates, mineral oils and the like.

In the literature products have already been described having the structure:

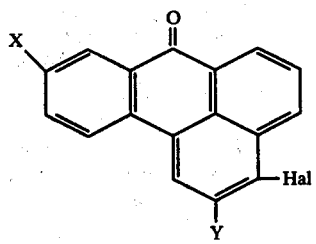

(II)

wherein
A = the anthraquinone or benzanthrone residue;
X = —NH— or —S—;
Y = —S— or —O—; and
Z = halogen.

These products may be employed a pigments for paints, printing inks, and various plastic materials.

Likewise compounds are known having the following structure:

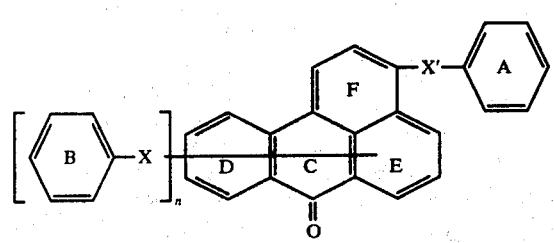

(III)

wherein rings A, B, D, E may be substituted with various substituents, except —SO₃H;
X and X' are, independently, either O or S; and
n = 0 or 1.

These compounds are dyes suited for the dyeing of acetylated cellulose, polyesters, polyamides, and polyolefines.

It has now been found (in accordance with the present invention) that benzimidazolic dyes having the structure (I) display dyeing power and light fastness consideraby higher than in the case of broadly similar compounds, for instance benzothiazolic or thiophenolic dyes falling under structures (II) and (III).

Dyes of the present invention are particularly suitable for the bulk dyeing of polystyrene, ABS, rigid PVC, polymethylmethacrylate, polyethylene, polycarbonate, mineral oils, and the like.

These dyes are prepared by heating benzanthronic halogen derivatives of structure (IV) together with 2-mercaptobenzimidazole (V) in dipolar aprotic solvents, and in the presence of suitable acidity acceptors, according to the reaction scheme:

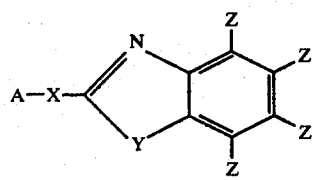 + 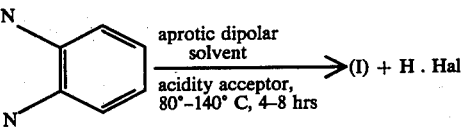

(IV)              (V)

wherein
-X and -Y have the meanings already indicated above for (I); and
—Hal = —Br or —Cl.

Intermediates having structure (IV), which are known per se and which are used for the preparation of the dyes of this invention, are e.g. 3-bromo-benzanthrone, 3,9-dibromo-benzanthrone, 2-methoxy-3-bromo-benzanthrone and 2-methoxy-3,9-dibromo-benzanthrone. Moreover, these intermediates are easily available or synthesizable according to per se well known techniques. For instance, intermediate (IV) may be prepared by bromination with Br₂ of benzanthrone in nitrobenzene solvent.

Intermediate (V), used in the synthesis of dyes having the structure (I), is available on the market or synthesizable according to per se known techniques, for instance from reaction of orthophenylenediamine with carbon sulphide and potassium hydroxide.

The dipolar aprotic solvents that may be conveniently used for the preparation of dyes having structure (I) are, amongst others: dimethylformamide, dimethylacetamide, dimethylsulfoxide, 1-methylpyrrolidine-2-one and hexamethylphosphotriamide, separately or in admixture with each other.

As acidity acceptors there may be used, for instance, anhydrous sodium carbonate or potassium carbonate or organic bases, such as pyridine or piperidine, also separately or in admixture with each other.

The reaction temperatures may vary from 80° C to about 140° C.

The reaction times may vary from 4 to about 8 hours.

The application of the dyes of this invention on or with plastic materials is carried out by directly mixing together, in a suitable mixer, the dye and the plastic or resin in either powdery or granulated form, and in the presence or absence of dulling agents, depending on the degree of transparency desired.

The mixture thus obtained is subjected to a homogenizing treatment either by calendering or by passing it through an extruder at the temperature best suited for each type of plastic or resin in the molten state.

For instance, in the case of polystyrene the homogenizing is carried out in an extruder at 190°-200° C. Thereupon the plastic material coming from the extruder is transformed into granules in suitable cutting machines and is then subjected to the desired molding operations, for instance in a conventional injection molding press under substantially conventional techniques.

When the dyes, which are object of this invention, are incorporated into a substrate in the absence of dulling agents such as $TiO_2$, there are obtained perfectly transparent manufactured articles. In the presence of $TiO_2$, there are obtained full and pure tones that range from yellow to orange. The dyes may for brevity be referred to as "plastosoluble", by which is meant that they are readily soluble, miscible or dispersible in the plastic materials or mineral oils with which they are to be associated as fluorescent dyes.

The overall fastnesses of the products of formula (I), especially the fastness to light and to heat treatment, are excellent.

The particular brightness imparted to the above materials by the dyes of the present invention may be explained by the considerable fluorescence that said dyes display when dissolved in the plastic material that acts as a solvent.

The particularly high dyeing power that is to be found in the products, according to this invention, are directly connected to the value of the molecular extinction coefficient in solution, which, in the case of this invention, is significantly greater than that of analogous dyes with other substituents according to known technique.

The examples that follow are given for purely illustrative purposes and in no way limit the scope of the invention. Examples 5 and 6, by the way, are for the sake of comparison with the prior art.

EXAMPLE 1

6.18 g. of 3-bromobenzanthrone, 4.65 g of 2-mercaptobenzimidazole, 3.13 g of anhydrous sodium carbonate, and 50 ml of dimethylformamide (DMF) were refluxed for 2 hours. The mixture was thereupon cooled down to room temperature, filtered, washed with a little DMF and then with boiling water, and finally dried in an oven.

In this way there were obtained 3.1 g of raw product wherein $X=Y=H$ in formula (I). This was crystallized from o-dichlorobenzene, thereby obtaining 2.8 g of a pure yellow-orange powder which, applied to the plastic materials according to the procedures of Ex. 4 below, resulted in a very intense yellow-green dyeing with a considerable yellow fluorescence.

The per cents found on analysis is in good agreement with the indicated structure:

| Calculated % | Found % |
|---|---|
| C = 76.2 | 76.0 |
| H = 3.7 | 3.5 |
| N = 7.5 | 6.8 |
| S = 8.5 | 8.6 |

EXAMPLE 2

4.10 g of 3,9-dibromobenzanthrone, 4 g of 2-mercaptobenzimidazole, 4.2 g of anhydrous sodium carbonate, and 50 ml of DMF were heated in a nitrogen atmosphere at 100° C for 8 hrs. The mixture was left to cool down to room temperature and was then filtered by washing with a little DMF, then with hot water, and finally with methanol. The whole was then dried.

There were obtained in this way 1.8 g of raw dye wherein $X=Br$ and $Y=H$ in the general formula (I). This was then crystallized from o-dichlorobenzene. The pure crystallized dye, applied to the plastic materials as described below in Example 4, gave a very intense yellow dyeing with a considerable yellow fluorescence.

The per cent analysis is in good agreement with the indicated structure.

EXAMPLE 3

1.68 g of 2-methoxy-3-bromobenzanthrone, 1.3 g of 2-mercaptobenzimidazole, and 1.56 g of anhydrous sodium carbonate were admixed with 30 ml of dimethylformamide (DMF), and this system was then put under a nitrogen atmosphere.

The mixture was heated up to 100°-110° C and kept under stirring at this temperature for 8 hours. Thereupon, and after cooling down to room temperature, the mass was filtered and washed with DMF, then with hot water until neutrality was attained, and finally with methyl alcohol. Thereafter it was crystallized from o-dichlorobenzene, thereby obtaining 0.7 g of a yellow-orange powdery product wherein $X=H$ and $Y=OCH_3$ in the general formula (I).

The product, applied to plastic materials as described below in Example 4, gave a yellow-orange dyeing of great intensity and with a considerable yellow fluorescence.

The per cent analysis was in good agreement with the indicated structure.

EXAMPLE 4

0.04 g of the dye of the general formula (I), pre-dispersed and homogenized with 100 g of polymethylmethacrylate in a rotating drum for 48 hours, were heat-treated at 100° C for one night.

The polymer or resin, dried in the charging hopper of the extruder, was extruded at a temperature of 190°-220° C. The material coming from the extrusion, after granulation, was then thoroughly dried and then injection-molded at a temperature between 220° and 330° C.

The manufactured article thus obtained was subjected to fastness tests in accordance with UNI Standards (Ente Nazionale Italiano Unificazione) corresponding to the A.A.T.C.C. of the USA.

The fastness characteristics in all cases turned out to be from good to excellent, in particular the light fastness.

The granulated material, when subjected to heat stability tests by extrusion in runs of 1 minute, at temperatures between 220° and 300° C, in general displayed excellent heat stability.

EXAMPLE 5

This is a comparative test with a compound of known structure of type (II).

0.04 g of a dye having the following structure:

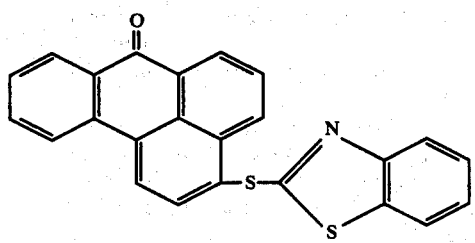

were applied to 100 g of polymethylmethacrylate, following the procedure described above in Example 4.

In this way there was achieved a pale-yellow dyeing of decidedly lower strength than that obtained with the dyes of general formula (I), as well as a medium fluorescence strength.

EXAMPLE 6

This is a comparison test with a compound of known structure of (III).

0.04 g of a dye having the following structure:

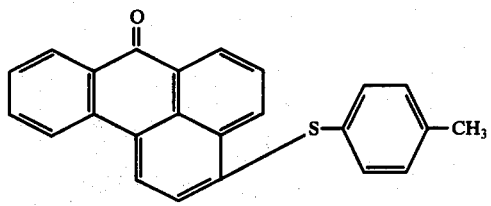

were applied to 100 g of polymethylmethacrylate, following exactly the same procedure as described above in Example 4.

There resulted a yellow dyeing with strength considerably lower than that of the dyes of structure (I) and slightly lower than that of the dye as applied in Example 5.

The observed fluorescence was about equal to that of the dye as applied in Example 5, but considerably lower than that of the dyes of structure (I).

From the preceding examples the following conclusions may be drawn:

Taking into consideration the structure of the general formula (VI), comprising structures (I), (II) and (III):

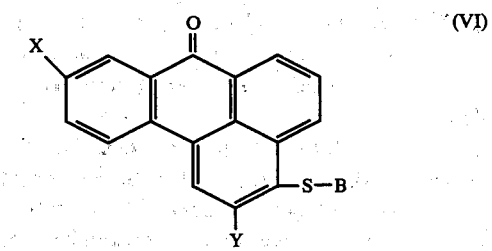

wherein -X and -Y have the meaning specified for structure (I) and B is a 2-benzothiazolyl (II) or a formula (III) residue, it is possible to draw up the following comparative table that illustrates especially well the above said characteristics of the exemplified dyes:

| Example | 1 | 2 | 3 | 5 | 6 |
|---|---|---|---|---|---|
| Structure | (I) | (I) | (I) | (II) | (III) |
| X | —H | —Br | —H | —H | —H |
| Y | —H | —H | —OCH$_3$ | —H | —H |
| B | benzimidazolyl | benzimidazolyl | benzimidazolyl | benzothiazolyl | p-tolyl |
| λmax.,mμ (DMF) | 470 | 480 | 490 | 400 | 430 |
| ε(DMF) | 20,000 | 19,500 | 18,400 | 14,600 | 10,600 |
| tone of fluorescence | Deep Yellow | Deep Yellow | Deep Yellow | Medium Yellow | Medium Yellow |
| Tone of manufactured article (polymethylmethacrylate | Yellow Green | Yellow | Yellow Orange | pale Yellow | pale Yellow |
| S.L. (polymethylmethacrylate) | 5–6 | 4–5 | 4–5 | 2 | 3–4 | wherein
X, Y and B have the meanings shown in the table;
λmax. = wave length (in mμ) of maximum absorption in the visible spectrum (determined by the spectrophotometric method);
S.L. = Fastness to light measured according to UNI Standards (Ente Italiano Unificazione) corresponding to the A.A.T.C.C. Standards in the USA;
ε = molecular extinction coefficient; and
DMF = dimethylformamide.

Observing the preceding table, it will be noticed how the presence of the benzimidazolic group in the dyes which are the object of this invention results in a considerable rise in quality as far as dyeing power and type of fluorescence are concerned, in comparison with the benzothiazolic derivatives and especially with respect to derivatives having structure (III). What is claimed is:

1. A plastosoluble fluorescent organic dye derived from benzanthrone, and having the general formula:

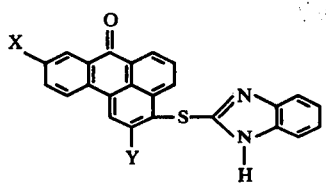

wherein
X = —H or —Br; and
Y = —H, —OCH₃ or —OC₂H₅.

2. The dye of claim 1, wherein X = Y = H.
3. The dye of claim 1, wherein X = Br and Y = H.
4. The dye of claim 1, wherein X = H and Y = OCH₃.
5. A process for the preparation of a dye of the general formula (I), as defined in claim 1, wherein a halogenated substituted benzanthrone of structute (IV) as shown herein is heated with 2-mercaptobenzimidazole (V) in a dipolar aprotic solvent, at a temperature of about 80° to about 140° C, and in the presence of an acidity acceptor.
6. A process according to claim 5, wherein as dipolar aprotic solvent there is used at least one compound selected from the class consisting of dimethylformamide, dimethylacetamide, dimethylsulphoxide, 1-methylpyrrolidine-2-one and hexamethylphosphotriamide.
7. A process according to claim 5, wherein as acidity acceptor there is used at least one compound selected from the class consisting of anhydrous sodium carbonate, anhydrous potassium carbonate and organic bases.
8. A process according to claim 7, wherein as acidity acceptor there is used an organic base selected from the class consisting of pyridine and piperidine.
9. The use of dyes of general formula (I), as defined in claim 1, in the bulk dyeing of polystyrene, polymethylmethacrylate, rigid PVC, polyethylene, acrylonitrile/butadiene/styrene copolymers, polycarbonates or mineral oils.
10. A bulk-dyed polystyrene, polymethylmethacrylate, rigid PVC, polyethylene, acrylonitrile/butadiene/styrene copolymer, polycarbonate or mineral oil, wherein the dye has the general formula (I) as defined in claim 1.

* * * * *